(12) United States Patent
Bouhnik et al.

(10) Patent No.: US 9,084,542 B2
(45) Date of Patent: Jul. 21, 2015

(54) APPARATUS AND METHODS FOR COMPUTED TOMOGRAPHY IMAGING

(75) Inventors: Jean-Paul Bouhnik, Zichron Yaacov (IL); Yaron Hefetz, Kibbutz alonim (IL)

(73) Assignee: General Electric Company, Schenectady, NY (US)

( * ) Notice: Subject to any disclaimer, the term of this patent is extended or adjusted under 35 U.S.C. 154(b) by 491 days.

(21) Appl. No.: 12/616,043

(22) Filed: Nov. 10, 2009

(65) Prior Publication Data

US 2011/0110486 A1    May 12, 2011

(51) Int. Cl.
| | |
|---|---|
| A61B 6/00 | (2006.01) |
| A61B 6/03 | (2006.01) |
| A61B 5/00 | (2006.01) |
| A61B 6/04 | (2006.01) |
| A61B 6/02 | (2006.01) |

(52) U.S. Cl.
CPC .................. *A61B 6/032* (2013.01); *A61B 6/037* (2013.01); *A61B 6/4241* (2013.01); *A61B 6/482* (2013.01); *A61B 6/503* (2013.01); *A61B 6/5205* (2013.01); *A61B 6/5235* (2013.01); *A61B 6/5247* (2013.01); *A61B 5/7289* (2013.01); *A61B 6/027* (2013.01); *A61B 6/0457* (2013.01); *A61B 6/541* (2013.01)

(58) Field of Classification Search
CPC ....... A61B 6/0457; A61B 6/541; A61B 6/027
See application file for complete search history.

(56) References Cited

U.S. PATENT DOCUMENTS

| | | | |
|---|---|---|---|
| 4,998,268 A | 3/1991 | Winter | |
| 5,224,135 A | 6/1993 | Toki | |
| 5,386,452 A | 1/1995 | Toki | |
| 5,499,283 A | 3/1996 | Toki | |
| 6,229,869 B1 | 5/2001 | Hu | |
| 6,266,553 B1 | 7/2001 | Fluhrer et al. | |
| 6,275,562 B1 | 8/2001 | He et al. | |
| 6,404,841 B1 | 6/2002 | Pforr et al. | |
| 6,519,314 B1 * | 2/2003 | Baba et al. | 378/19 |
| 6,539,074 B1 | 3/2003 | Yavuz et al. | |
| 6,628,742 B2 | 9/2003 | Pan et al. | |

(Continued)

FOREIGN PATENT DOCUMENTS

| | | |
|---|---|---|
| JP | 2004509692 A | 4/2004 |
| JP | 2009056229 A | 3/2009 |

(Continued)

OTHER PUBLICATIONS

Search Report and Written Opinion from PCT/US2010/050810, Mar. 10, 2011.

(Continued)

*Primary Examiner* — Hoon Song
(74) *Attorney, Agent, or Firm* — Dean D. Small; The Small Patent Law Group, LLC.

(57) ABSTRACT

Apparatus and methods for computed tomography (CT) imaging are provided. One method includes providing a patient table to move along an examination axis of a rotating gantry of a CT imaging system having at least one imaging detector. The imaging detector includes a pixelated detector array. The method further includes configuring the CT imaging system to perform an overlapping helical CT scan by controlling a speed of the moving patient table along the examination axis through a field of view (FOV) of the at least one imaging detector of the rotating gantry.

12 Claims, 8 Drawing Sheets

(56) References Cited

U.S. PATENT DOCUMENTS

| | | |
|---|---|---|
| 6,801,594 B1 | 10/2004 | Ali et al. |
| 7,113,570 B2 | 9/2006 | Toth et al. |
| 7,382,858 B2 | 6/2008 | Gohno |
| 7,421,057 B2 | 9/2008 | Watanabe |
| 7,480,362 B2* | 1/2009 | Carmi ............... 378/19 |
| 2002/0025018 A1* | 2/2002 | Takagi et al. ............ 378/8 |
| 2002/0118790 A1* | 8/2002 | Pan et al. ............ 378/8 |
| 2004/0264626 A1 | 12/2004 | Besson |
| 2004/0264627 A1* | 12/2004 | Besson ............... 378/5 |
| 2005/0069081 A1* | 3/2005 | Kokubun et al. ........ 378/15 |
| 2007/0116171 A1 | 5/2007 | Hsieh et al. |
| 2007/0217568 A1* | 9/2007 | Edic et al. ............ 378/4 |
| 2008/0253505 A1* | 10/2008 | Imai ............... 378/8 |

FOREIGN PATENT DOCUMENTS

| | | |
|---|---|---|
| JP | 2009142518 A | 7/2009 |
| WO | 2009/081316 A1 | 7/2009 |

OTHER PUBLICATIONS

Unofficial English translation of JP Office Action issued Mar. 11, 2014 in connection with corresponding JP Application No. 2012-538817.

* cited by examiner

APPARATUS AND METHODS FOR COMPUTED TOMOGRAPHY IMAGING

BACKGROUND OF THE INVENTION

The subject matter disclosed herein relates generally to diagnostic imaging systems, and more particularly to computed tomography (CT) diagnostic imaging systems.

In conventional gated CT imaging, for example, in gated cardiac CT imaging, each imaging view in each image slice acquired by the CT imaging system has to include all of the phases of the gating (e.g., gated image information for one complete cardiac cycle) to generate proper clinically relevant images. In cases where only the systole phase is imaged, all image views of each image slice must include valid systole data to generate proper images. Additional rotations are sometimes needed to fill in an empty imaging view where no image information was acquired. Some rotations may also include invalid data due to a bad electrocardiogram (ECG) signal. As a result of these errors and the need for additional gantry rotations, an increase in x-ray dose to the patient, an increase in time of acquisition and/or an increase in image artifacts may result.

In step and shoot imaging system where the patient is imaged while stopped at different axial locations, a loss of imaging time results due to the table motion, in particular having no image data acquired during table motion. Additionally, conventional detector arrays require high power x-ray sources that expose the patients to higher levels of radiation.

When imaging using CT imaging systems have two-dimensional (2D) detectors of arrays, several slices may be imaged during a single rotation, thereby reducing acquisition time. However, non-central slices are imaged in a slightly oblique axial angle resulting in difficulty during image reconstruction, image artifacts and/or non-uniform image quality among the image slices.

BRIEF DESCRIPTION OF THE INVENTION

In accordance with various embodiments, a method for providing computed tomography (CT) imaging includes providing a patient table to move along an examination axis of a rotating gantry of a CT imaging system having at least one imaging detector. The imaging detector includes a pixelated detector array. The method further includes configuring the CT imaging system to perform an overlapping helical CT scan by controlling a speed of the moving patient table along the examination axis through a field of view (FOV) of the at least one imaging detector of the rotating gantry.

In accordance with other embodiments, a computer readable medium for controlling a computed tomography (CT) imaging scan is provided. The computer readable medium is programmed to instruct a computer to perform a slow-rotating CT scan using at least one pixelated Cadmium Zinc Telluride (CZT) two-dimensional (2D) detector array and generate an overlapping helical scan data set based on the slow-rotating CT scan.

In accordance with yet other embodiments, a computed tomography (CT) imaging system is provided that includes a rotatable gantry having a bore therethrough and at least one two-dimensional pixelated imaging detector coupled to the rotatable gantry. The CT imaging system further includes a movable patient table configured to move along an examination axis through the bore of the rotatable gantry and a controller configured to control a speed of the movable table through the bore along the examination axis to perform an overlapping helical CT scan using the at least one pixelated imaging detector rotating about the bore.

DETAILED DESCRIPTION OF THE INVENTION

Figure 1:
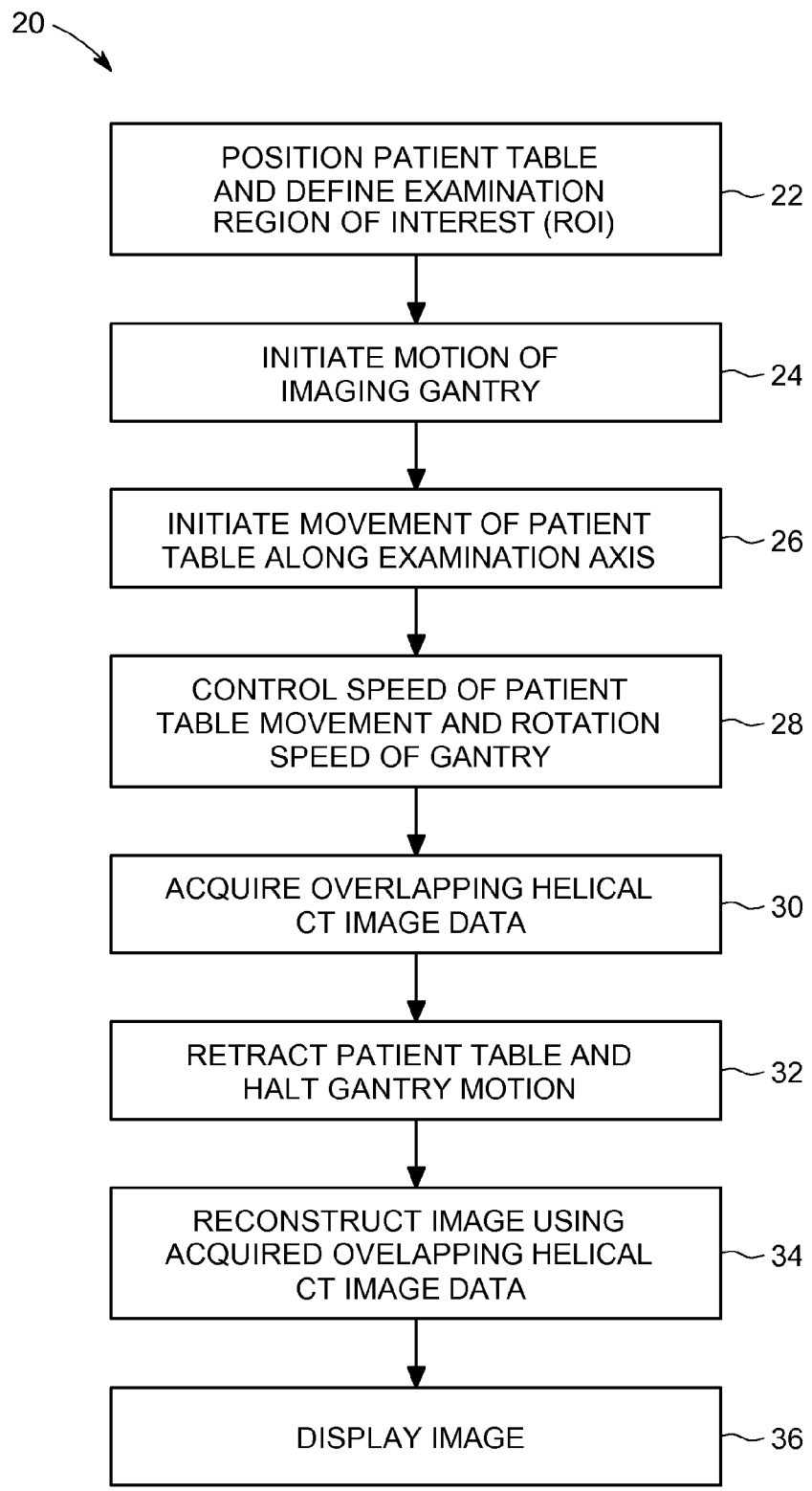
FIG. 1 is a flowchart of a method for controlling an imaging system in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide methods and systems for controlling the movement of an imaging system, and in particular, the gantry and/or patient table to oversample a portion or volume of a patient. For example, in computed tomography (CT) imaging, the speed of the gantry and/or patient table is controlled to provide an overlapping helical scan, and in particular partial overlap, wherein the pitch of the helix is a fraction of the number of rows of the detector array of the imaging system.

At least one technical effect of the various embodiments is that the resulting reconstructed images may have reduced or eliminated bad pixel artifacts realized by the practice of some embodiments of the described systems and techniques. Moreover, larger detectors with a large number of defective cells may be used. Additionally, the imaging systems can have lower maintenance requirements as a result of the various embodiments accommodating or tolerating new bad pixels that did not exist at the time of system install. Moreover, there is a lower likelihood of the need for repeated imaging scans due to bad gating problems and the gantry does not need to rotate at higher speed. Further, a lower power x-ray tube may be used with the various embodiments. The various embodiments also operate using an imaging system that uses a slower rotating speed gantry and in cardiac applications may not need to use beta-blockers (e.g., tachycardia conditions) during cardiac imaging.

In some embodiments an overlapping helical scan is performed using two-dimensional (2D) solid state detectors arrays, such as Cadmium Zinc Telluride (CZT) 2D detector arrays capable of acquiring transmission and optionally also emission information. It should be noted that although the various embodiments are described in connection with a multi-modality imaging system, the various embodiments may be implemented in a single modality computed tomography (CT) imaging system. The different imaging modalities may include, for example, Positron Emission Tomography (PET), Single Photon Emission Computed Tomography (SPECT), an ultrasound system, Magnetic Resonance Imaging (MRI) or any other system capable of generating tomographic images. In some exemplary embodiments, the dual modality imaging system is a Nuclear Medicine (NM)/CT imaging system, such as a SPECT/CT or PET/CT imaging system.

Specifically, a method 20 for controlling an imaging system, such as a SPECT/CT imaging system is illustrated. The method 20 includes positioning a patient table and defining an examination region of interest (ROI) of the imaging system at 22. The positioning can include both manual and electronically controlled movement. For example, as shown in the exemplary dual modality imaging system 50 illustrated in FIG. 2, a patient table 52 on which a patient 54 is supported may be moved, for example, in an up-down direction, in-out direction (e.g., advancing the patient along the examination axis toward a bore 56 of a gantry 58) and optionally also a right-left direction. In some embodiments a controller unit 60 controls the movement and operation of the various components of the imaging system 50. It should be noted that the movement of the various components may be controlled electronically using motors connected to the components. However, in some embodiments, some of the components may not be moved using motors, but instead manually positioned by an operator. It should be noted that although the method 20 is described in connection with the dual modality imaging system 50 of FIG. 2, the method 20 may be implemented with different types of imaging systems as described in more detail herein.

In some embodiments, the controller unit 60 includes a table controller 62 that controls movement of the patient table 52 to position the patient 54 relative to an initial field of view (FOV) of one or more imaging detectors 70, which are illustrated as a pair of solid-state two-dimensional (2D) detector arrays, for example, a pair of CZT detector arrays. Each of the imaging detectors 70 is configured as an independent imaging detector capable of detecting transmission and emission information. In other embodiments, only a single imaging detector 70 may be used in connection with the method 20 or additional imaging detectors 70 may be used.

Once the patient 54 is aligned with the bore 56, for example, a head (or feet) of the patient 54 is adjacent the front opening of the bore 56, an imaging scan procedure is initiated. This procedure may include initiating an automatic imaging protocol sequence for performing a particular scan, for example, a gated SPECT/CT cardiac scan, may be initiated by a user, or a combination thereof. Referring again to the method 20 of FIG. 2, as part of the scan initiation process, motion of the gantry 58 is initiated at 24, which may be performed using a gantry motor controller 64. Once the gantry 58 is operating such that the imaging detectors 70 are rotating about the bore 56 at a predetermined examination speed as described in more detail below, movement of the patient table 52 is initiated at 26, for example, by the table controller 62. In particular, movement of the patient table 52 into the bore 56 along the examination axis is initiated.

The initiation of movement of the gantry 58 and imaging detectors 70 begins an overlapping helical scan in accordance with various embodiments. For example, in a cardiac imaging scan, the initiation of movement at 24 and 26 begins an overlapping helical gated CT scan, which acquires phase gated cardiac information using ECG leads 80 that are joined to the patient 54 to detect cardiac activity. The leads 80 are joined to the patient prior to initiation of movement of the gantry 58 and imaging detectors 70 and generates ECG signals that are digitized, processed, filtered and the like, by an ECG processor module 82, which allows, for example, the acquisition of gated cardiac SPECT/CT data and synchronized rotation of the gantry 58 as described in more detail herein. The ECG processor module 82 may provide the ECG signals to a processing unit 90 and/or to an image reconstruction processor 92. Alternatively, the ECG processor module 82 may process the ECG signals and output to the processing unit 90 and/or to the image reconstruction processor 92 time stamps associated with particular points in the cardiac cycle associated with image information acquired by a data acquisition system (DAS) 96 that receives electrical signal data produced by the one or both of the imaging detectors 70.

The processing unit 90 and/or the image reconstruction processor 92 associates the time stamps or ECG signals with corresponding projection data sets to identify the cardiac activity at the time at which an associated projection data set is obtained and/or to control the speed of the gantry 58. Alternatively, one of the processing unit 90 and/or to the image reconstruction processor 92 may generate, based on the ECG signal, a time stamp.

Figure 2:
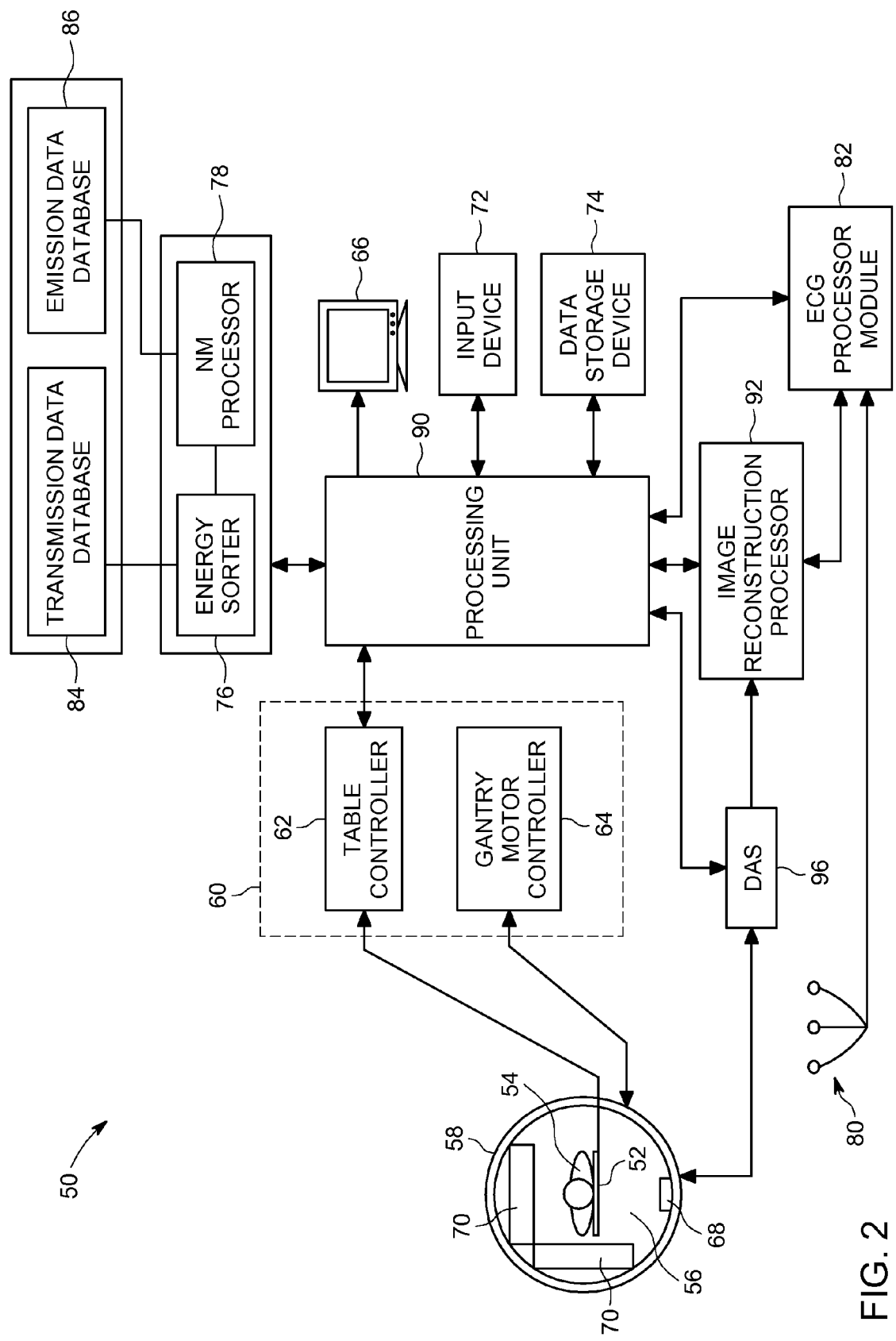
FIG. 2 is a block diagram of an imaging system that can be controlled by the method of FIG. 1.

Referring again to the method 20 of FIG. 2, the overlapping helical imaging scan is acquired using various embodiments that control at 28 the speed of the movement of the patient table 52 (e.g., translation of the patient table 52 into the bore 56 or extension of a portion of the patient table 52 into the bore 56) and/or the rotation speed of the gantry 58. In particular, the movement of the patient 54 along the examination axis through the bore 56 of the gantry 58 (and through one or more FOVs) is controlled and/or the speed of rotation of the gantry 58, which corresponds to the rotation speed of the imaging detectors 70 about the patient 54 is controlled. In various embodiments, the control of speed of the movement of the patient table 52 and/or rotation of the imaging detectors 70 results in an overlapping helical scan (where the patient table 52 and the imaging detectors 70 are constantly moving) that provides an oversampling of the image data for the patient 54. For example, the various embodiments provide an overlapping helical scanning wherein the pitch of the helix is a fraction of the number of rows in the detector array (e.g., pixelated CZT detector array) forming the imaging detectors 70. The amount of overlap, and accordingly, the amount of oversampling is controlled based on the speed of at least one of the movement of the patient table 52 and rotation of the imaging detectors 70.

Figure 3:
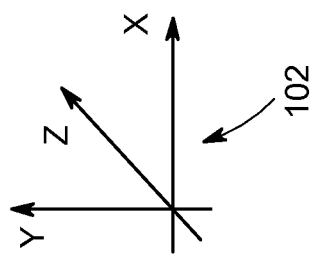
FIG. 3 is a diagram of a gantry of an imaging system illustrating control of rotation speed based on gating in accordance with various embodiments.
Figure 3:
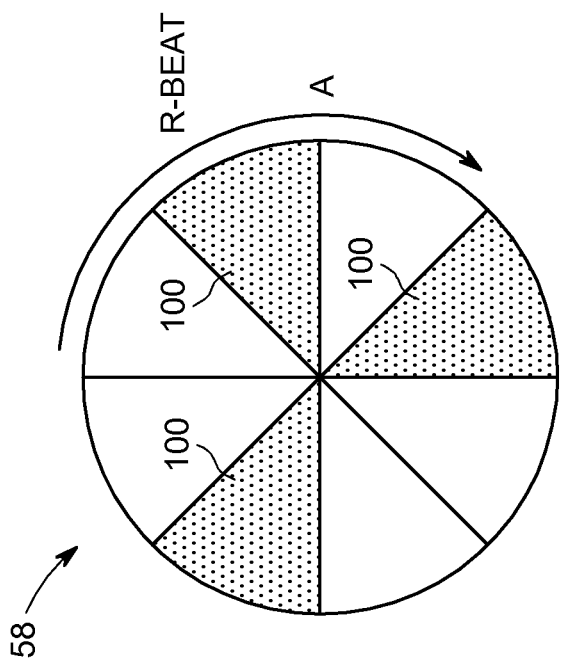

In a gated cardiac imaging scan, the control of speed of the movement of the patient table 52 and/or rotation of the imaging detectors 70 can provide a slow rotating photon counting dual threshold CZT based CT imaging scan. Moreover, gating information from the ECG signals may be used to control, for example, the rotation velocity of the imaging detectors 70 (and optionally the speed of movement of the patient table 52). For example, as shown in FIG. 3, the gantry 58 is controlled such that the rotation velocity of the imaging detectors 70 is timed or synchronized to the ECG signals, for example, the R-beat (also referred to as the R-wave) of the ECG signals. In cardiac applications, the NM data is also ordered in projections for each of a plurality of gates that are used to divide the cardiac cycle based on, for example, the ECG signals over time. The ECG signal is often referred to as a PQRST waveform that is acquired using the ECG leads 80 (e.g., ECG electrodes) and represents cardiac cell activity in the myocardium of the heart.

Accordingly, as shown in FIG. 3, the rotation speed of the imaging detectors 70 may be controlled such that each rotation of the imaging detectors 70 is synchronized with a plurality, for example, three R-beats. Accordingly, each volume of the patient 54 is sampled a plurality of times. As an example, in order to synchronize the rotation velocity of the imaging detectors 70 based on R-beats illustrated by the sectors 100 in FIG. 3, the following control parameters may be used:

1. For a patient having a heart rate of about 60 beats per minute (BPM)
2. Gantry rotation velocity of 22 revolutions per minute.
3. Each R-beat corresponds to 135 degrees per rotation of the gantry 58 as illustrated by the arrow A in FIG. 3.

It should be noted that exact synchronism to the R-beat is not always possible, for example in a cardiac patient having irregular heart beats. However, various embodiments may still be performed using the slow rotating CT scan as described herein.

It also should be noted that the movement of the patient table 52 in various embodiments may also be coordinated or synchronized to move the patient 54 to provide image acquisition oversampling, and which may be synchronized with the rotation speed of the gantry 58. In accordance with various embodiments, the speed of the movement of the patient table 52 is controlled such that overlapping helical scanning is provided wherein the pitch of the helix is a fraction of the number of rows in the detector array to acquire overlapping helical CT image data at 30 in the method 20 of FIG. 2. For example, if the imaging detectors 70 each comprise pixelated CZT detector arrays formed from N=16 rows array, in various embodiments a pitch of p=4 rows is provided. Accordingly, each patient volume is sampled at least four times.

More particularly, a datum of image information may be identified by: R, V, D, wherein R is the Rotation Number, V is the View Number and D is the Detector Number; given as D={r,c} wherein r is the row number (r=1, 2, . . . , 16) and c is the column number. In accordance with the various embodiments, using oversampling, a specific Line of Sight (LOS), appears not as a single datum [R,V,r,c], but appears as "N/p" data points: [R,V,r,c]; [R+1,V,r+p,c]; [R+2,V,r+2*p,c]; [R+N/p,V,D,r+(N/p−1)*p,c].

Figure 4:
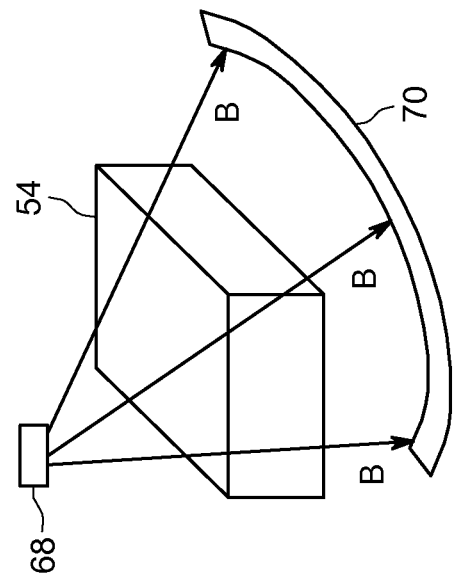
FIG. 4 is a diagram illustrating computed tomography (CT) imaging in a transmission detection mode in accordance with various embodiments.

Accordingly, because each LOS is seen N/p times, even if a bad pixel (e.g., pixel not operating properly) in an imaging detector 70 is part of the LOS for one data point, the bad pixel likely will not be in each of the data points for the same oversampled LOS. Thus, as shown in FIG. 4, wherein the imaging detector 70 is operating in a transmission detection mode to detect x-rays from a radiation source, such as an x-ray source 68 (e.g., x-ray tube) also mounted to the gantry 58 (as illustrated in FIG. 2), a helical overlapping scan is provided wherein for each volume area or slice of the patient 54 (the coordinate system for the patient 54 is illustrated by the coordinate system 102) multiple datum sets for each LOR is acquired by different portions of the imaging detector 70 as illustrated by the arrows B.

Figure 5:
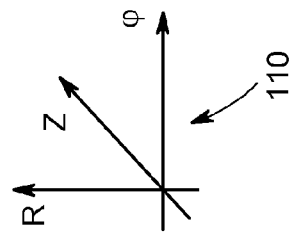
FIG. 5 is a diagram illustrating cone beam CT imaging in accordance with various embodiments.
Figure 5:
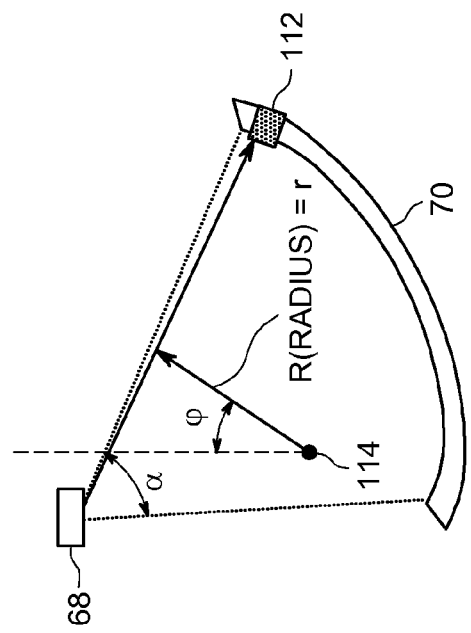

As another example, for cone beam CT imaging in accordance with various embodiments, as illustrated in FIG. 5, the Sinogram coordinates are defined by: R, ö, z, è, shown by the coordinate system 110. In the coordinate system 110, è is the (relatively small) incline angle, and the following is provided:

R=>{0-maximum reconstructed radius};
z=>{length of the reconstructed length of the volume+the inclination compensation}
ö=>{0-180 deg}; thus a 180+á gantry rotation requirement is used)
è=>{−max incline−max incline}
g=>{gates, 1, 2, . . . N}

Figure 6:
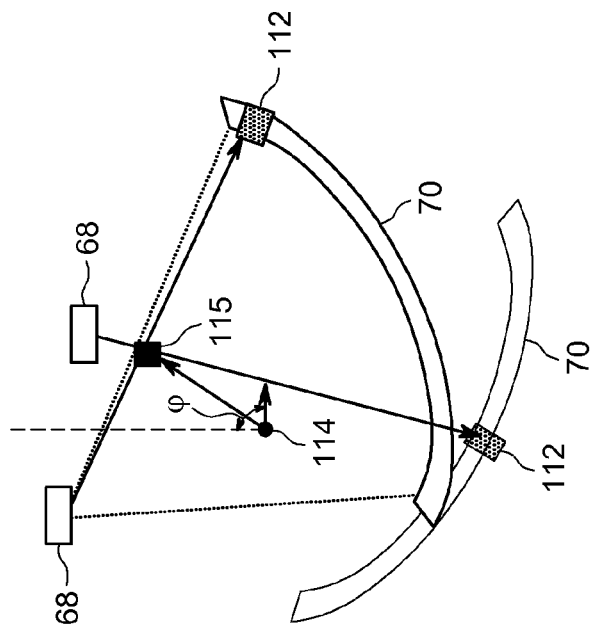
FIG. 6 is a diagram illustrating overlapping helical CT scanning in accordance with various embodiments.

In operation, using the ECG signal as described herein to provide gated imaging, the phase of the heart beat is divided to sections or phases, for example, eight phases. The total designation of a datum is {R, ö, z, è, g}. As illustrated in FIG. 5, it is apparent that that a particular pixel 112 of the imaging detector 70, for example, pixel "j" probes only a specific radius "r" of the sonogram space about a center of rotation 114. If this pixel is bad, the entire R=r "line" in the sonogram space is completely missing. However, as described in more detail herein, in accordance with various embodiments, and using an overlapping helical scan, data may be summed or averaged or combined, which may be performed in a weighted averaging or other combining process, to compensate for bad pixels (or the bad pixel information may be ignored or discarded). It should be noted that compensation for other lost or unreliable pixel data may provided, for example, using the oversampling methods to compensate for lost data due to a bad cardiac gate. For example, as shown in FIG. 6, as the imaging detector 70 rotates about the gantry 58 (shown in FIG. 2), a voxel 115 corresponding to a volume unit of the patient 54 is imaged using different pixels 112 of the imaging detector 70. Thus, in various embodiments, each LOS is sampled at positive and negative oblique angles and close to normal angles.

Figure 7:
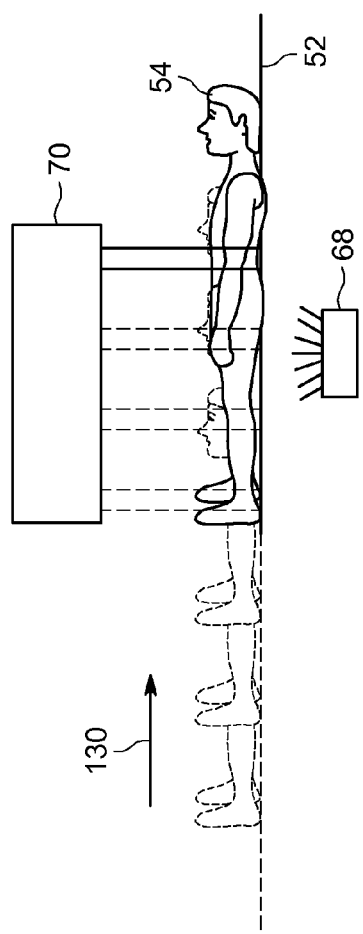
FIG. 7 is a diagram illustrating patient table movement in accordance with various embodiments.

Accordingly, as a patient 54 moves along the examination axis (which may be along the patient axis), which movement in various embodiments is a continuous movement (which may or may not be constant), for cardiac gate imaging, each rotation of the imaging detectors 70 about the patient 54 corresponds to multiple cardiac cycles. Additionally, the speed of the patient table 52 is controlled such that a portion of the patient 54 moves through the FOV of the imaging detector after a plurality of rotations, for example, two, three, four, five or more time, thereby providing oversampling of the patient volume as shown in FIG. 7. It should be noted that the patient 54 may also move through the entire FOV of the imaging detectors 70 in fractional rotations, for example, two and a half rotations of the imaging detectors 70. Accordingly, as illustrated in FIG. 7, a same volume of the patient 54 is imaged by a plurality of pixel rows (four rows are illustrated) as the patient 54 is moved along an examination axis 130 through the FOV of the imaging detectors 70. It also should be noted that only one imaging detector 70 is shown in the transmission detector mode of FIG. 7 wherein the imaging detector 70 detects x-rays impinging on a detector face thereof that passes through the patient 54 from the x-ray source 68.

Figure 8:
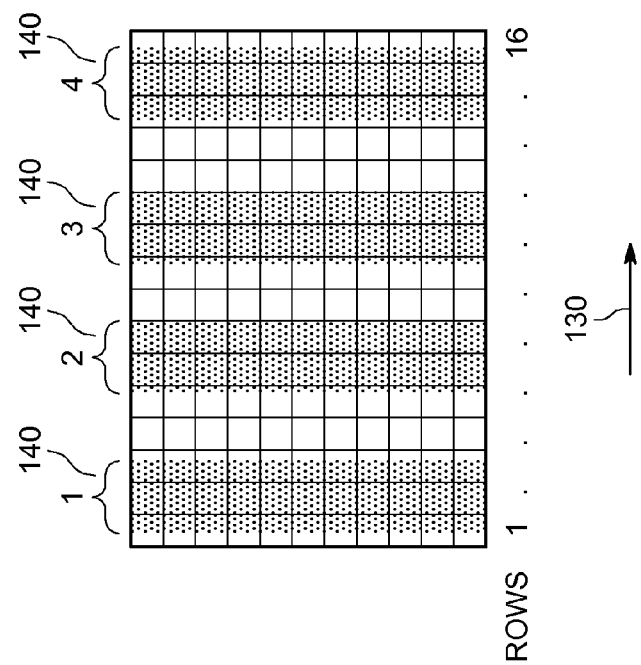
FIG. 8 is a diagram illustrating oversampling using a detector array of an imaging detector in accordance with various embodiments.

In other embodiments, emission data (e.g., photon emissions) may be detected by the pair of imaging detectors 70 configured in different arrangements (e.g., L-mode or H-mode) and operating in a similar manner to provide oversampling. Thus, the patient volume is imaged multiple times, illustrated as four times by four different sections 140 of the imaging detector (identified by the darkened pixels) as illustrated in FIG. 8.

Figure 9:
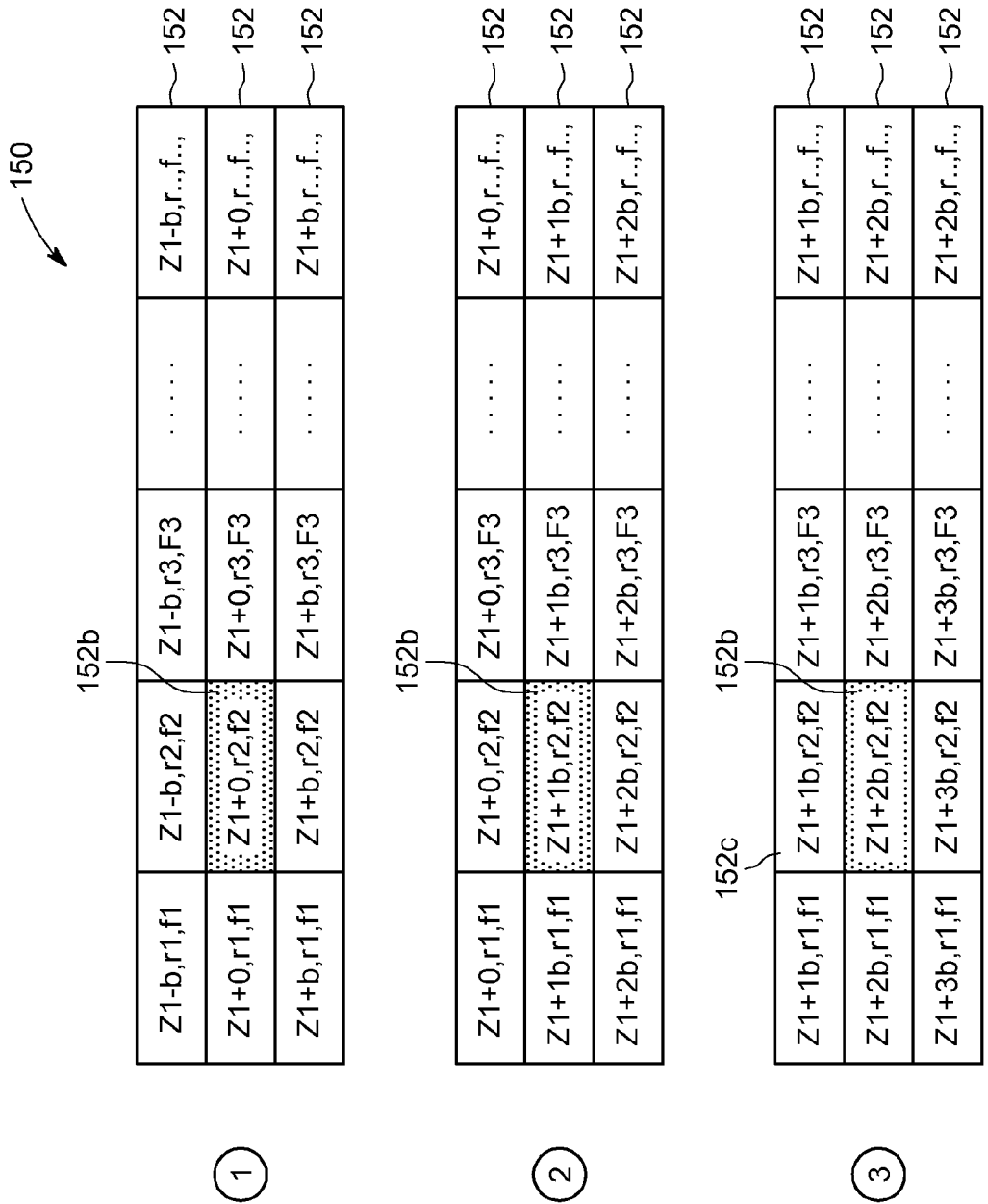
FIG. 9 is a diagram illustrating image data detection by pixels of an imaging detector using overlapping helical scanning in accordance with various embodiments.

Accordingly, an as shown in FIG. 9, with the overlapping helical scan performed by different embodiments, a volume of the patient is oversampled such that different pixels acquire image data for the same volume. In particular, FIG. 9 illustrates a multi-row (three rows are shown), also referred to as a multi-slice, detector 150 having a plurality of pixels 152. The detector 150 is illustrated in an initial position at 1, after patient table motion and a full gantry rotation at position 2 and after additional patient table motion and another full gantry rotation at position 3. As illustrated, the same portion of a patient, for example, a same volume of a patient is imaged at different rows of pixels 152 of the detector 150 at each of the positions. Thus, as can been seen, a bad pixel 152b acquires image data from different regions of the same portion of the patient. Thus, as the patient table advances, the bad pixel is accounted for by image data acquired by another pixel 152c that images the same region of the portion of the patient that was previously imaged by the bad pixel.

Referring again to the method 20 of FIG. 1, after the overlapping helical CT image data is acquired, the patient is removed from the bore 56 of the imaging system 50. In various embodiments, at 32 the patient table 52 is retracted from the bore 56 such that the patient 54 can be removed from the patient table 52. Thereafter, or optionally while the overlapping helical CT image data is acquired, one or more images are reconstructed at 34 using the acquired overlapping helical CT image data. The image(s) may be reconstructed by the image reconstruction processor 92 using known reconstruction techniques. For example, if the CT image data set is a transmission data set, the data set may be processed to reconstruct a three-dimensional (3D) image that corresponds to a plurality of 2D slices taken through the organ of interest. In one embodiment, for example, the 3D image may be reconstructed using a filtered back-projection or an iterative reconstruction technique. The filtered back-projection technique (or the iterative reconstruction technique) converts attenuation measurements from a scan into integers called "CT numbers" or "Hounsfield units", which are used to control the brightness of a corresponding pixel. The reconstructed slices are then combined to form the 3D image of the organ of interest.

The reconstructed image may thereafter be displayed at 36. For example, cardiac image data, which may be reconstructed cardiac image data stored in a data storage device 74 (e.g., a memory) may be displayed as a cardiac image on a display 66 of the imaging system 50. It should be noted that the data storage device 74 may include stored data, which may be stored either short term (e.g., during processing) or long term for later retrieval. CT images may further be used in a multi-modality imaging system to correct the emission image, for example for attenuation and optionally for scatter of the emitted photons by the patient tissue.

Figure 10:
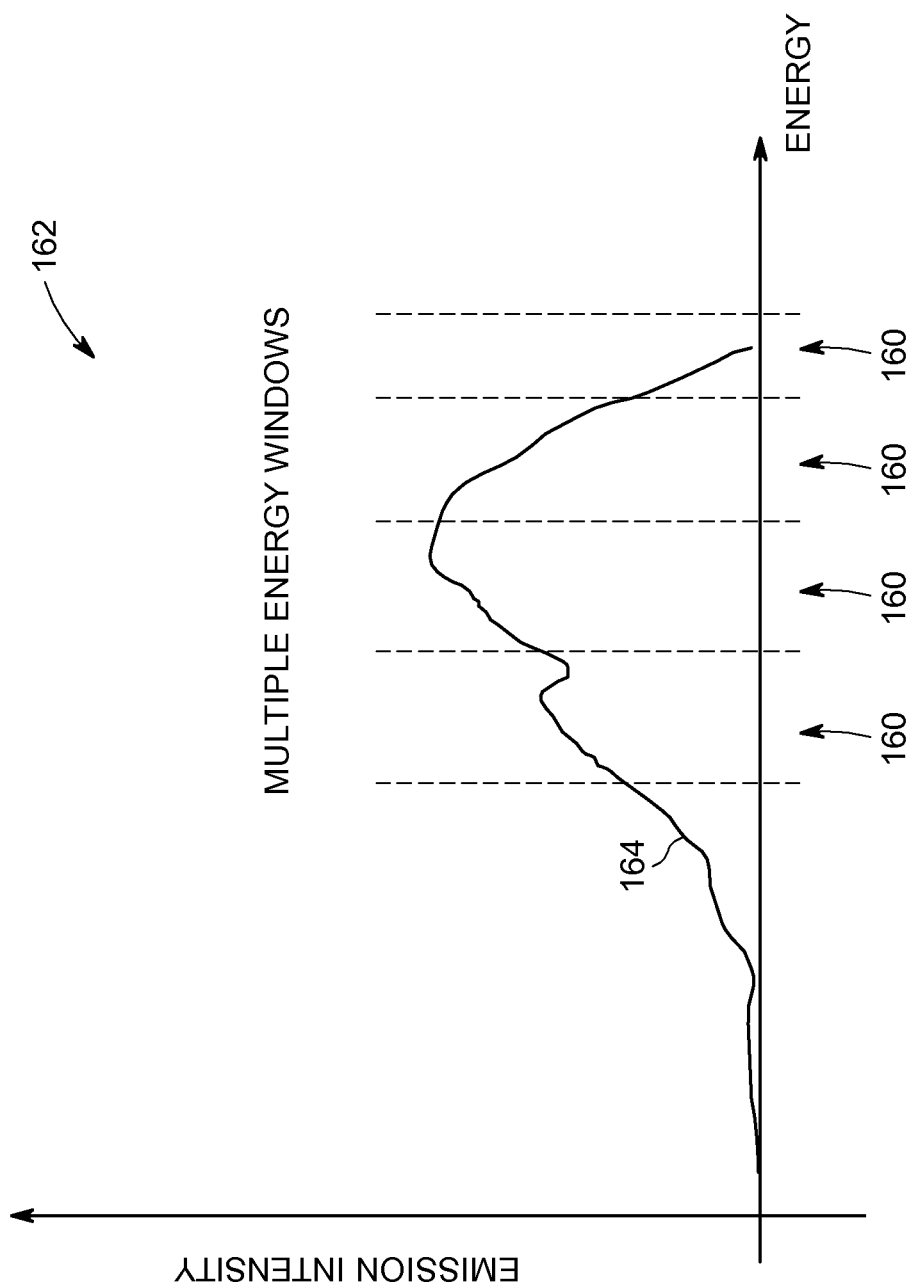
FIG. 10 is a graph illustrating an emission intensity curve with a plurality of energy windows in accordance with various embodiments.

Using the overlapping helical scanning, different detector configurations and operations may be provided. For example, a multi-threshold detector may be provided such that photons are counted in each of a plurality of energy windows 160 as shown in the graph 162 of FIG. 10 illustrating a an emission intensity curve 164. In the graph 162, the vertical axis represents emission intensity and the horizontal axis represents energy level. Accordingly, for example, for cardiac imaging using different absorbers for imaging with radiopharmaceuticals in combination with R+R cardiac gating, two good R-waves are likely acquired for each cardiac cycle using the overlapping helical scan of the various embodiments. Thus, because the cardiac cycle is defined such that a good R+R cardiac cycle is determined, the image data acquired in that cardiac cycle may be used and does not have to be discarded or ignored as bad image data.

Figure 11:
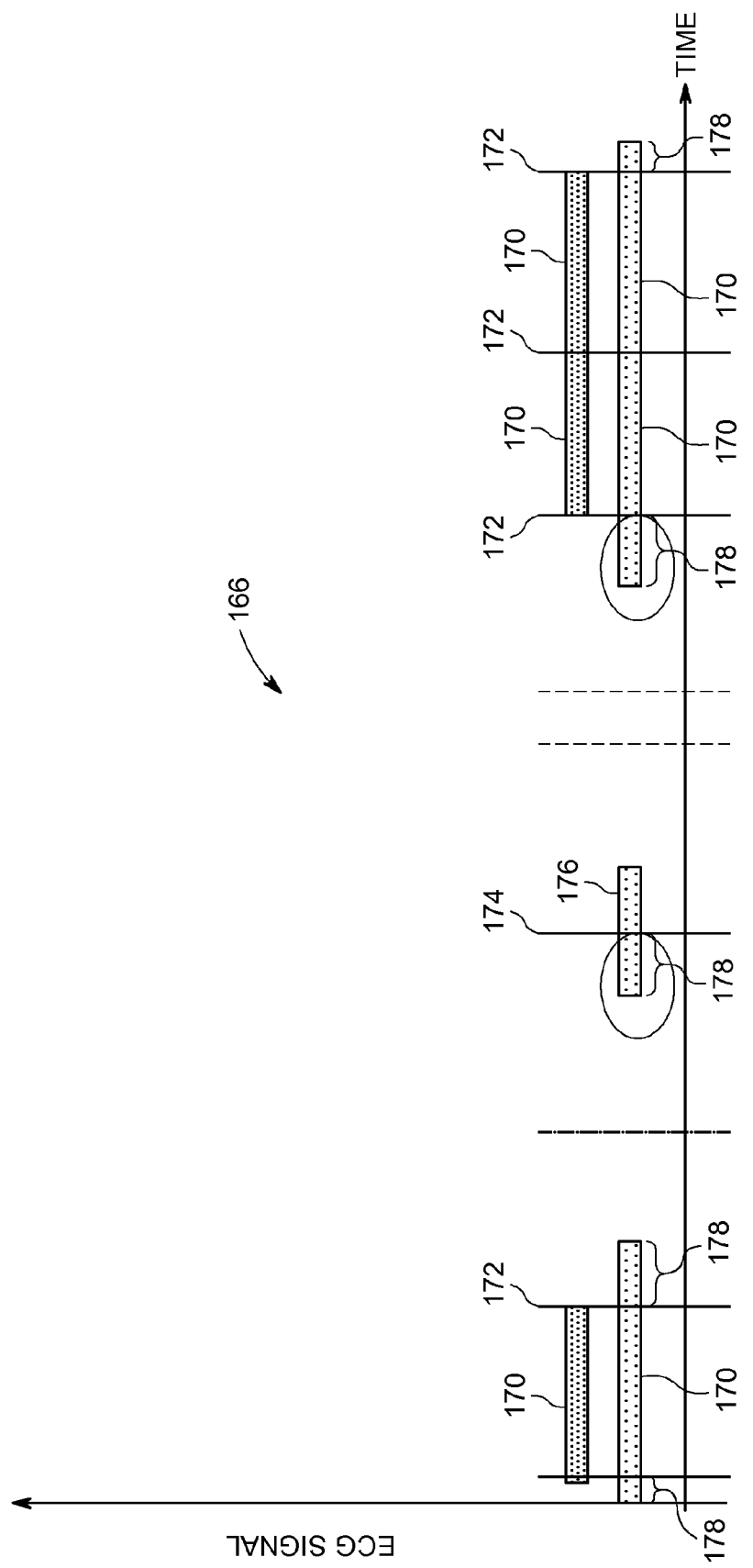
FIG. 11 is a diagram illustrating retrospective gating in accordance with various embodiments.

In gating methods of the art, only data acquired between two consecutive R-waves 172 as illustrated in FIG. 11 are used, which data is identified by the time interval 170 in FIG. 11. As can be seen, each missing, defective, or un-identified R beat causes loss of data acquisition in two cardiac cycles, namely the one before and the one after the unidentified beat. According to some embodiments, data after an identified R bit (R-wave) is collected for at least a period of time even if the following beat is missing, defective or otherwise unidentified. Similarly, according to other embodiments, data before an identified R bit (R-wave) is collected for at least a period of time even if the preceding beat is missing, defective or otherwise unidentified. Additionally, according to still other embodiments, data before an identified R bit (R-wave) is collected for at least a period of time even if the preceding beat is missing, defective or otherwise unidentified and data after an identified R bit (R-wave) is collected for at least a period of time even if the following beat is missing, defective or otherwise unidentified.

Thus, once a good R-wave is detected, the various embodiments use image data slightly before and slightly after the start of the good R-wave. For example, as shown in the graph 166 of FIG. 11, retrospective gating may be provided. The vertical axis of the graph 166 represents the ECG signal and the horizontal axis represents time. In particular, various embodiments, during a cardiac scan, determine whether the heart was previously in a relaxed state (the start of an R-wave, which may be time stamped by gating as described herein), and uses image data acquired slightly before and/or after the identified R-wave (e.g., 2/10 of a second) during image reconstruction as the heart is necessarily at rest during this time period. In particular, the data in the time intervals 170 is conventionally identified as corresponding to good R-waves 172. For example, in accordance with various embodiments, such as wherein data before an identified R bit (R-wave) is collected for at least a period of time even if the preceding beat is missing, defective or otherwise unidentified and data after an identified R bit (R-wave) is collected for at least a period of time even if the following beat is missing, defective or otherwise unidentified, when an isolated good R-wave 174 is identified, data corresponding thereto was not discarded and an additional data set 176 is acquired. Additionally, using retrospective gating, additional data 178 prior to and after the R-wave is also acquired. Accordingly, in the illustrated example, one and half times more valid data is acquired.

If the imaging system 50 as shown in FIG. 2 is a dual modality imaging system, the DAS 96 is configured to receive electrical signal data produced by the imaging detectors 70 and which may be, for example, transmission and/or emission data. Also, a user input device 72 (e.g., keyboard, mouse, trackball, etc.) may be provided to receive user input for controlling the imaging system 50.

It should be noted that one or more functions related to one or more of data acquisition, motion control, data processing and image reconstruction may be accomplished through software or hardware, and by shared processing resources, which may be located within or near the imaging system 50, or may be located remotely.

Thus, in a dual modality imaging configuration the imaging detectors 70 each have a gamma emission and radiation detection face that may be directed towards a structure of interest within the patient 54 or towards the x-ray source 68. In the various embodiments, the actual FOV for each of the imaging detectors 70 may be increased, decreased, or relatively unchanged by the type of collimator used, such as pinhole, parallel-beam converging, diverging fan-beam, converging or diverging cone-beam, multi-bore, multi-bore converging, multi-bore converging fan-beam, multi-bore converging cone-beam, multi-bore diverging, or other types of collimators.

The systems and methods, thus, may be performed using multi-modality medical diagnostic imaging systems capable of scanning using different modalities, such as, for example, but not limited to, PET/CT or SPECT/CT. The term "multi-modality" refers to systems that perform scans in different modalities, but the various embodiments may be implemented in connection with single modality imaging systems.

Thus, in accordance with various embodiments, an overlapping helical scan is performed wherein the patient is moved while image is acquired. Such a system generates an overlapping helix, for example, from a fan beam helical scan. The overlapping helix mapped out by, for example, a fan beam yields projection data from which images in each prescribed slice may be reconstructed. It should be noted that reconstruction methods for helical scanning typically use helical weighing methods that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a 2D slice taken through the object as described in more detail herein.

In various embodiments, the volume of interest may be selected by a user and the processing unit 90 controls the imaging system 50 to acquire the transmission data (and/or emission data). In various embodiments, thus, the imaging system 50 is controlled to perform, for example, at least one of a CT scan, a PET transmission scan, and a CT scout scan to acquire the transmission data or a PET or SPECT scan to acquire photon emission data. It should be noted that the x-ray source 68 may be used to acquire image data and/or attenuation data.

Various processors, sorters, and databases are used to acquire and manipulate emission and transmission data. In a dual modality configuration, the processors, sorters and databases of the imaging system 50 include an energy sorter 76, an NM processor 78, a transmission data database 84 and an emission data database 86. In some embodiments, the energy sorter 76 provides time, location, and energy data to the NM processor 78. The NM processor 78 generally uses the received data to identify pairs of data, also known as coincidence pairs, coincident pair lines and lines of response, corresponding to annihilation events that occurred inside the region of interest for PET imaging and uses received gamma radiation from inside the region of interest for SPECT imaging. After the annihilation event or gamma photon is identified, the emission data database 86 is updated accordingly to store information relating to the annihilation event or gamma photon detection. Additionally, transmission information may be stored in the transmission data database 84, which information may be different types of information, such as image information, attenuation information, etc.

After image acquisition is performed, sets of transmission and emission are stored in databases 84 and 86, respectively, and image reconstruction processor 92 uses the stored information to generate images that may be requested, for example, by a system operator.

Thus, various embodiments provide overlapping helical scanning using a slow-rotating gantry with a CZT based 2D detector. By using slow, overlapping (such as partially overlapping) helical scanning, gating to ECG is possible without high speed rotors (and use of beta-blockers in tachycardia, which necessitates a physician in the examination room). Also, the slow, partially overlapping helical scanning allows the use of detector arrays in imaging detectors with multiple bad cells without artifact. Defect free detector modules in CZT detectors are expensive due to low production yield. Additionally, replacing a module due to a malfunction of a single or few pixels is costly. By employing the various embodiments of the methods of overlapping helical scanning, artifact free imaging may be provided using lower cost detectors with some defective pixels. Additionally, maintenance cost may be reduced by tolerating several defects.

Photon counting also allows a reduction of x-ray source power and reduction of total dose. Dual (or multi) energy photon counting further allows for calcium scoring (which may be performed without using a dual or multi energy x-ray source or repeated scanning). The various embodiments also allow for improved attenuation correction (e.g., differentiation of bone from soft tissue) and reduced x-ray scatter effects and optionally correction of beam hardening.

Additionally, noise reduction and bad cell tolerance may be achieved by combining data from neighboring cells in columns and rows. Improved retrospective gating and iterative reconstruction also allows for artifact-free reconstruction even with some missing data.

Variations and modifications to the various embodiments may be provided, for example, imaging detectors having different sized pixelated arrays may be used and/or the speed of movement of the patient table 52 or the speed of rotation of the imaging detectors 70 may be changed. For example, using a sixteen slices detector, and two rows per revolution of patient table advance, each voxel in the image is sampled eight times (e.g., oversampled). Thus, there is an increased probability of having image samples including one or more datum that are accurate, for example, without bad pixels.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for providing computed tomography (CT) imaging, the method comprising:
    acquiring gated cardiac information by sensing electrocardiogram (ECG) signals over multiple cardiac cycles;
    providing a patient table to move along an examination axis of a rotating gantry of a CT imaging system having at least one imaging detector, the imaging detector including a pixelated detector array;
    configuring the CT imaging system to perform an overlapping helical CT scan by controlling a speed of the moving patient table along the examination axis through a field of view (FOV) of the at least one imaging detector of the rotating gantry and a rotation speed of the rotating gantry to be synchronized with gated cardiac information, wherein each rotation of the rotating gantry is synchronized to occur within a select number of—cardiac cycles for a patient being imaged, wherein the select number is at least three; and
    configuring the CT imaging system to adjust the speed of the moving patient table based on a heart rate of the patient as indicated by the ECG signals.

2. A method in accordance with claim 1 wherein the speed of the patient table is controlled such that a pitch of a helix of the overlapping helical scan is a fraction of a number of rows of the pixelated detector array.

3. A method in accordance with claim 1 further comprising configuring the CT imaging system to control the speed of the moving patient table to sample a volume of a patient supported on the moving patient table at least three times.

4. A method in accordance with claim 1 further comprising configuring the CT imaging system to perform multiple energy photon counting using the at least one imaging detector.

5. A method in accordance with claim 1 further comprising configuring the CT imaging system to perform retrospective gating to acquire additional valid image data based on detected cardiac R-wave events.

6. A method in accordance with claim 1 wherein the pixelated detector arrays comprises a Cadmium Zinc Telluride (CZT) two-dimensional (2D) array.

7. A method in accordance with claim 1 wherein the CT imaging system comprises a dual-modality imaging system.

8. A method in accordance with claim 1 further comprising coordinating movement of the patient table and the rotating gantry to perform an overlapping helical scan, wherein a patient is sampled a plurality of times by the at least one imaging detector.

9. A method in accordance with claim 1 wherein the at least one imaging detector rotates such that a voxel corresponding to a volume unit of a patient is imaged using different pixels of the at least one imaging detector, wherein each line of sight is sampled at positive and negative oblique angles, and at least one approximately normal angle.

10. A method in accordance with claim 9 wherein a volume of the patient is imaged a plurality of times by different sections of the at least one imaging detector;
   detecting unreliable pixel data from a first section of the at least one imaging detector; and
   compensating for the unreliable pixel data using data from a second section of the at least one image detector.

11. A method in accordance with claim 1, further comprising acquiring the gated cardiac information with a multi-threshold detector, wherein collected photons are counted in a plurality of energy windows, wherein two or more R-waves are detected for each cardiac cycle.

12. A method in accordance with claim 1, further comprising acquiring additional cardiac information at least one of before or after an identified R-wave if a corresponding preceding or following beat is at least one of missing, defective, or unidentified, and using the additional cardiac information to reconstruct an image.

* * * * *